United States Patent [19]

König et al.

[11] Patent Number: 4,478,828

[45] Date of Patent: Oct. 23, 1984

[54] NONAPEPTIDE HAVING IMMUNOSTIMULATIVE ACTIVITY, PROCESS FOR THE PREPARATION THEREOF, AND ITS USE

[75] Inventors: Wolfgang König, Hofheim am Taunus; Rolf Geiger, Frankfurt am Main; Rainer Obermeier, Hattersheim am Main; Hubert Müllner, Kelkheim, all of Fed. Rep. of Germany

[73] Assignee: Hoechst Aktiengesellschaft, Frankfurt am Main, Fed. Rep. of Germany

[21] Appl. No.: 508,589

[22] Filed: Jun. 28, 1983

[30] Foreign Application Priority Data

Jun. 30, 1982 [DE] Fed. Rep. of Germany ........ 3224379

[51] Int. Cl.³ .................... A61K 37/00; C07C 103/52
[52] U.S. Cl. ............................. 424/177; 260/112.5 R
[58] Field of Search .................. 260/112.5 R; 424/177

[56] References Cited

U.S. PATENT DOCUMENTS

| 4,229,438 | 10/1983 | Fujino et al. | 260/112.5 R |
| 4,404,133 | 9/1983 | Yanaihara et al. | 260/112.5 R |
| 4,415,493 | 11/1983 | Weigle et al. | 260/112.5 R |

Primary Examiner—Delbert R. Phillips
Attorney, Agent, or Firm—Finnegan, Henderson, Farabow, Garrett & Dunner

[57] ABSTRACT

The invention provides a nonapeptide of the formula I $$\boxed{\text{Glu}}\text{-Asp-Ser-Ser-Ser-Thr-Gly-Trp-Asn-OH} \qquad (I)$$

a process for the preparation thereof and its use, furthermore intermediates for preparing a compound of the formula I.

4 Claims, No Drawings

NONAPEPTIDE HAVING IMMUNOSTIMULATIVE ACTIVITY, PROCESS FOR THE PREPARATION THEREOF, AND ITS USE

The invention provides a nonapeptide of the formula I

  (I)

(L-pyroglutamyl-L-aspartyl-L-seryl-L-seryl-L-seryl-L-threonyl-glycyl-L-tryptophyl-L-asparagine) and its physiologically tolerable salts with organic bases, alkali and alkaline earth metal ions, furthermore pharmaceutical products and the use thereof.

The invention provides furthermore a process for the preparation of this compound, which comprises liberating the protected peptide of the formula II

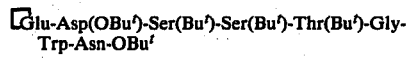  (II)

from the protective groups of the tert.-butyl type according to the methods usual in peptide chemistry for tryptophane-containing peptides (see for example R. Geiger and W. König in E. Gross and J. Meienhofer, The Peptides, Academic Press, New York 1981, p. 82).

In addition to the antiviral activity, interferons have also an immunomodulating effect (Steward, W. E., The Interferon System, Springer, New York, 1979).

Surprisingly, the nonapeptide of the formula

  (I)

which corresponds to a partial sequence of the human fibroblast interferon (Nature 285, 542–547, 1980) has a considerable immunostimulative effect in in vitro tests. The synthesis of the peptide of the formula II is carried out by means of segment coupling from three dipeptides and one tripeptide (see synthesis scheme). For the peptide condensation the dicyclohexyl-carbodiimide/1-hydroxybenzotriazole (DCC/HOBt) method is applied (with the exception of the ⌐Glu-Asp(OBu$^t$)-OH synthesis).

⌐Glu-Asp(OBu$^t$)-OH is prepared by reaction of pyroglutamic acid-2,4,5-trichlorophenyl ester ( Glu-OTcp) with Asp(OBu$^t$) in the presence of 1-hydroxybenzotriazole as catalyst. The side chain functions and the C-terminal carboxyl group are blocked as tert.-butyl ether (Bu$^t$) or tert.-butyl ester (OBu$^t$). The benzyloxycarbonyl radical (Z) which can be split off selectively by catalytic hydrogenation in the presence of tert.-butyl esters or tert.-butyl ethers serves for intermediately protecting the amino functions. The carboxyl groups of two segments are temporarily protected by methyl (OMe) or ethyl esters (OEt). These esters are stable in the catalytic hydrogenation, but they can be selectively split off by alkali in the presence of protective groups of the tert.-butyl type.

The protective groups of the peptide of the formula II are split off by dissolving the substance in 90% trifluoroacetic acid. In order to prevent tert.-butylation of the tryptophane, a thiol is advantageously added, especially preferably 1,2-mercaptoethane.

Synthesis scheme:

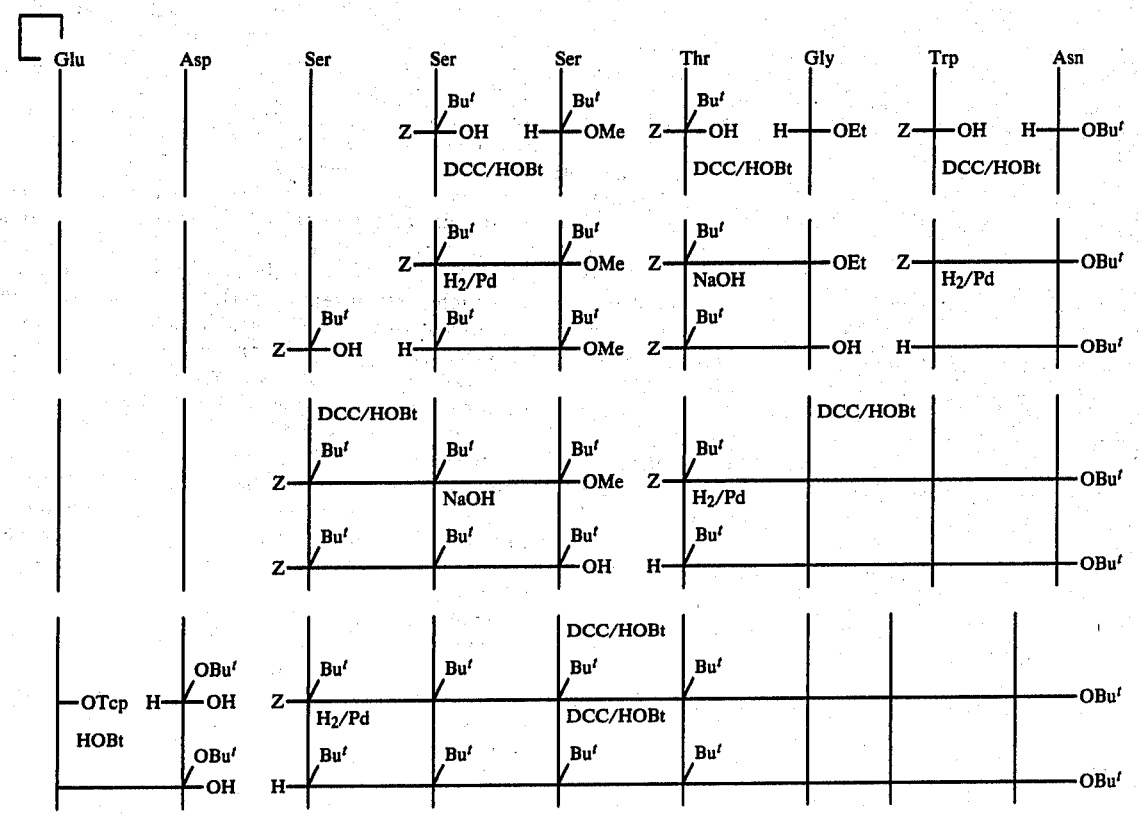

Synthesis scheme:

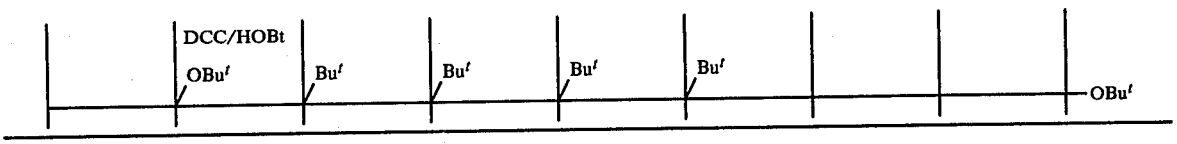

The nonapeptide of the invention was tested in the Plaqueforming Cell Assay (PFC test) and in the phythemagglutinin stimulation test (PHA test) for its lymphocyte-stimulative action.

In the PFC test, cell cultures of freshly dissected spleens of mice ($2 \times 10^7$ spleen cells per ml) were prepared in RPMI 1640 and 30 $\mu$l of fetal calf serum (FCS) per ml of cell culture. In vitro immunization is carried out with $5 \times 10^7$ sheep erythrocytes/ml. The test cell cultures are incubated daily with the corresponding dose of the test substance. After a test period of 5 days, the cells are centrifuged off, washed with RPMI 1640 medium, and the direct PCF test is carried out as follows: The cells are mixed in an agarose solution with a 10% sheep erythrocyte suspension, and poured onto a plane surface. In the gel layer so formed the stimulated lymphocytes set free antibodies in the subsequent incubation which diffuse in the environment and adhere to the sheep erythrocytes present in these places. After addition of guinea pig complement the red blood cells lyse. Light-colored, circular spots are formed in the reddish-brown gel, which can be discerned with a naked eye, and which are the hemolysis halos of the plaques. In the center of such hemoylsis halos there is an antibody-producing cell. The number of lymphoid cells which form specific immunoglobulins can therefore be equalized with the plaque values found.

The PHA test allows conclusions on the amount of mature, that is, stimulable, lymphocytes by means of the function test on stimulability with the phytolectin PHA. The lectin, like bacterial or viral antigens, incites the lymphocytes to a blast transformation. It causesd proliferation either directly or by induction of lymphokine secretion.

The incorporation of radioactive thymidine within a defined period of time is then the measure for the number of stimulated cells. The mature or immunologically potent T cells only are stimulated. Thus, the influence of a substance on the maturation of lymphocytes can be observed by means of this test. However, stimulation must remain below the optimum; for, at a higher concentration other subpopulations of lymphocytes are stimulated, too, and the effect cannot be observed any longer. The peptide of the invention was added to the culture medium in varying concentrations.

In both test systems, stimulation of the lymphocytes by the nonapeptide of the invention depending on the dose is observed as a bell-shaped curve (see Tables 1 and 2)

Test results of the nonapeptide according to the invention:

TABLE 1

| | PFC test | | | | |
|---|---|---|---|---|---|
| | Control | 1 ng | 10 ng | 100 ng | 1 $\mu$g | 5 $\mu$g/ml |
| Plaques/$10^6$ cells | 768 | 908 | 1112 | 1024 | 817 | 802 |

TABLE 2

PHA test (Addition of 20 $\mu$g PHA/ml Test time: 72 hours)

| Concentration of nonapeptide ($\mu$g/ml) | Incorporation of $^3$H—thymidine (cpm) | Stimulation index SI |
|---|---|---|
| control | 114 311 | |
| 5.0 | 107 670 | 0.94 |
| 1.0 | 113 978 | 1.00 |
| 0.5 | 143 831 | 1.26 |
| 0.125 | 137 519 | 1.20 |
| 0.0125 | 101 594 | 0.89 |

The compound of the invention may be applied for treating viral and fungoid immune deficiencies, long-term bacterial infections, autoimmune diseases, furthermore for the therapy of diseases caused by cells having immunologically relevant alterations of the cell membrane characteristics (for example tumor cells).

The invention relates furthermore to the use of the cited peptide quite geneally for influencing the maturation of T lymphocytes, and to agents containing this peptide as active ingredient.

The peptide of the invention can be adminstered intravenously, subcutaneously or intranasally. In the case of parenteral administration, the individual dose is from 0.01 to 10 mg (about 0.1 to 100 $\mu$g/kg/day), in the case of intranasal administration it is from 0.1 to 100 mg. The preferred dosage range in the case of parenteral administration is from 0.1 to 10, preferably 0.2 to 5, $\mu$g/kg/day. In serious cases it can be increased since toxic effects have not been observed hitherto. Decrease of the dose is also possible.

The compound of the invention can be administered intranasally or parenterally in a corresponding pharmaceutical formulation. For intranasal administration, the compound is mixed with the corresponding usual additives such as stabilizers or inert diluents, and according to known methods given a suitable administration form such as aqueous, alcoholic or oily suspensions or aqueous, alcoholic or oily solutions. Oily carriers or solvents are for example vegetable or animal oils, such as sunflower oil or cod-liver oil.

For subcutaneous or intravenous administration, the active compound or the physiologically acceptable salts thereof are given the form of solutions, suspensions or emulsions, if desired with addition of the corresponding usual substances such as solubilizers, emulsifiers or other auxiliaries.

Suitable solvents for the novel active compound and the corresponding physiologically tolerable salts are for example water, physiological saline solutions or alcohols such as ethanol, propanediol or glycerol, furthermore sugar solutions such as glucose or mannitol solutions, or a mixture of the cited different solvents.

The following Example illustrates the invention.

EXAMPLE (relative to the amount of solvent), suction-filtered, washed with water and dried over $P_2O_5$.

TABLE 3

Protected peptides prepared according to general procedure 1 and synthesis scheme.

| Peptide | Work-up Yield | M.p. °C. | $[\alpha]_D^{23}$ (c = 1) |
|---|---|---|---|
| Z—Trp—Asn—OBu$^t$ (crystallized from isopropanol/petroleum ether) | I 76% | 138–39 (in methanol) | −23.1° |
| Z—Ihr(Bu$^t$)—Gly—OEt (crystallized from petroleum ether | I 74% | 76 | +7.2° (in methanol) |
| Z—Thr(Bu$^t$)—Gly—Trp—Asn—OBu$^t$ (reprecipitated from ethyl acetate/petroleum ether) | I 89% | 111 | −19.9° (in methanol) |
| Z—Ser(Bu$^t$)—Ser(Bu$^t$)—Ser(Bu$^t$)—Thr(Bu$^t$)—Gly—Trp—Asn—OBu$^t$ (boiled with methanol) | II 81% | 234 | +7.0° (in trifluoroethanol) |
| Glu—Asp(OBu$^t$)—Ser(Bu$^t$)—Ser(bu$^t$)—Ser(Bu$^t$)—Thr(Bu$^t$)—Gly—Trp—Asn—OBu$^t$ (chromatography on silica gel in methylene chloride/methanol 9:1) | II 38% | 209–214 | +5.1° (in trifluoroethanol) |
| Z—Ser(Bu$^t$)—Ser(Bu$^t$)—OMe | I 85% | oil | |
| Z—Ser(Bu$^t$)—Ser(Bu$^t$)—Ser(Bu$^t$)—OMe (from petroleum ether) | I 76% | 113–115 | +22.4° (in methanol) |

1. General procedure for peptide coupling (Table 3)

10 mmols of an amino acid or peptide ester hydrochloride, 1.3 ml of N-ethylmorpholine, and 2.2 g of dicyclohexyl-carbodiimide (at 0° C.) are added to a solution of 10 mmols of a Z-amino acid or a Z-peptide and 1.35 g of 1-hydroxybenzotriazole in 10–100 ml of dimethylformamide or dimethylacetamide. The batch is stirred for 2–3 hours at 0° C., and subsequently abandoned overnight at room temperature.

Work-up I

The precipitate (dicyclohexyl urea) is suction-filtered, and the filtrate is concentrated. The residue is distributed between water and ethyl acetate. The ethyl acetate phase is shaken with saturated NaHCO₃ solution, KHSO₄/K₂SO₄ buffer and saturated NaHCO₃ solution in the indicated sequence, dried over Na₂SO₄, and concentrated. The residue is then triturated, generally with petroleum ether, and recrystallized from ethyl acetate/petroleum ether.

Work-up II (The substance precipitates in addition to dicyclohexyl urea): The batch is stirred with 10 ml of saturated NaHCO₃ solution and the about 5-fold amount of water

2. General procedure for the selective splitting-off of the benzyloxycarbonyl group (Table 4)

Depending on the solubility, 2.5 to 10 g of peptide are dissolved in about 150 ml of methanol or trifluoroethanol, or alternatively suspended. With N₂ flushing, Pd/carbon catalyst is added, and subsequently hydrogen is passed through the solution with stirring and addition of about 1–2N methanolic hydrochloric acid at pH 4.5 (autotitrator). When hydrochloric acid is no longer absorbed, the batch is flushed again with N₂, the catalyst is filtered off, and the filtrate is concentrated. The residue is usually triturated with ether and suction-filtered.

TABLE 4

Peptide ester hydrochlorides prepared according to general procedure 2

| Peptide ester hydrochloride | Yield | M.p. °C. | $[\alpha]_D^{23}$ (c = 1) |
|---|---|---|---|
| H—Trp—Asn—OBu$^t$.HCl hydrogenation in methanol | 96% | 108–110 | +7.1° (in methanol) |
| H—Thr(Bu$^t$)—Gly—Trp—Asn—OBu$^t$.HCl hydrogenation in methanol | 93% | 144–146 | −9.2° (in methanol) |
| H—Ser(Bu$^t$)—Ser(Bu$^t$)—OMe.HCl hydrogenation in methanol | 98% | oil | |
| H—Ser(Bu$^t$)—Ser(Bu$^t$)—Ser(Bu$^t$)—Thr(Bu$^t$)—Gly—Trp—Asn—OBu$^t$.HCl hydrogenation in trifluoroethanol | 93% | 176 (dec.) | +4.6° C. (in 80% acetic acid) |

3. General procedure for the saponification of peptide methyl esters (Table 5)

10 mmols of peptide are dissolved in 50 ml of dioxan/water 8:2. 11 ml of 1N NaOH are added with stirring, and agitation is continued for 1 hour room temperature. The batch is then neutralized with a small amount (1–2 ml) of 1N H₂SO₄, and concentrated. The residue is distributed with ice cooling between 10 ml of 1N H₂SO₄ and 50 ml of ethyl acetate. The ethyl acetate phase is washed with 10 ml KHSO₄/K₂SO₄ buffer and water in the indicated sequence, dried over Na₂SO₄ and concentrated. The dicyclohexylamine salts can be prepared from the residue in ether.

TABLE 5

| Z—peptides prepared according to general procedure 3 | | | |
|---|---|---|---|
| Peptide | yield | m.p. | $[\alpha]_D^{23}$ (c = 1) |
| Z—Thr(Bu$^t$)—Gly—OH | 99% | oil | |
| Z—Thr(Bu$^t$)—Gly—OH.dicyclohexylomine | 87% | 142° | +5.6° (in methanol) |
| Z—Ser(Bu$^t$)—Ser(Bu$^t$)—Ser(Bu$^t$)—OH | 69% | amorph. | +29.5° (in methanol) |

⌐Glu-Asp(OBu$^t$)-OH 3.4 g of ⌐Glu-OTcp are added to a suspension of 1.9 g (10 mmols) of H-Asp(OBu$^t$)-OH and 1.35 g of HOBt in 20 ml of dimethylformamide, the batch is stirred for several hours at room temperature and abandoned overnight. The following day, it is concentrated under highly reduced pressure, and the residue is triturated with ether. The precipitate is suction-filtered and washed with ether. Yield: 2.7 g. The substance contains still some HOBt and is therefore subjected to chromatography in 70% methanol on Sephadex ® LH 20 (column dimensions 100×4 cm).

Yield: 2.55 g (85%), m.p. 114°–159°, $[\alpha]_D^{23} = +1.9°$ (c=1, methanol).

⌐Glu-Asp-Ser-Ser-Ser-Thr-Gly-Trp-Asn-OH 850 mg (6.9 mmols) ⌐Glu-Asp(OBu$^t$)-Ser(Bu$^t$)-Ser(Bu$^t$)-Ser(Bu$^t$)-Thr(Bu$^t$)-Gly-Trp-Asn-OBu$^t$ are dissolved in a mixture of trifluoroacetic acid, water and 1,2-dimercaptoethane (9:1:1). The batch is abandoned for 1 hour at room temperature, concentrated, and the residue is triturated with ether. Yield 650 mg. For purification, the substance is boiled in 30 ml of methanol, and after cooling to room temperature it is suction-filtered. Yield 430 mg (65%). Amino acid analysis (hydrolysis: 24 hours at 120° C. in 6N HCl):

| | Asp | Thr | Ser | Glu | Gly | Trp |
|---|---|---|---|---|---|---|
| Calculated: | 2 | 1 | 3 | 1 | 1 | 1 |
| found: | 1.94 | 0.86 | 2.61 | 1.00 | 1.04 | — |

Under the hydrolysis conditions, tryptophane is completely destroyed, serine and threonine are partially destroyed. This explains the complete absence of Trp and the reduced values of Ser and Thr. UV spectrum: characteristic absorption band for Trp at 270 nm. Peptide content according to amino acid analysis and UV spectrum:

95%. $[\alpha]_D^{23} = -34.9°$ (c=1, in saturated NaHCO$_3$ solution).

What is claimed is:

1. Nonapeptide of the formula I

⌐Glu-Asp-Ser-Ser-Ser-Thr-Gly-Trp-Asn-OH   (I)

(L-pyroglutamyl-L-aspartyl-L-seryl-L-seryl-L-seryl-L-threonyl-glycyl-L-tryptophyl-L-asparagine) and its physiologically tolerable salts with organic bases, alkali and alkaline earth metal ions.

2. A method of influencing the maturation of T lymphocytes by administering an effective amount of a nonapeptide according to claim 1 or a pharmaceutically acceptable salt thereof.

3. A method of treating viral and fungoid immune deficiencies, long-term bacterial infections, autoimmune diseases or diseases caused by cells having immunologically relevant alteration of the cell membrane characteristics by administering an effective amount of a nonapeptide according to claim 1 or a pharmaceutically acceptable salt thereof.

4. A pharmaceutical composition for treating viral and fungoid immune deficiencies, long-term bacterial infections, autoimmune diseases or diseases caused by cells having immunologically relevant alteration of the cell membrane characteristics comprising an effective amount of a nonapeptide according to claim 1 or a pharmaceutically acceptable salt thereof and a pharmaceutically acceptable carrier.

* * * * *